United States Patent
Noack et al.

(10) Patent No.: US 9,285,169 B2
(45) Date of Patent: Mar. 15, 2016

(54) SINTERING DEVICE

(71) Applicant: Amann Girrbach AG, Koblach (AT)

(72) Inventors: Falko Noack, Lustenau (AT); Axel Reichert, Widnau (CH)

(73) Assignee: AMANN GIRRBACH AG, Koblach (AT)

( * ) Notice: Subject to any disclaimer, the term of this patent is extended or adjusted under 35 U.S.C. 154(b) by 3 days.

(21) Appl. No.: 14/356,293

(22) PCT Filed: Oct. 11, 2012

(86) PCT No.: PCT/AT2012/000256
§ 371 (c)(1),
(2) Date: May 5, 2014

(87) PCT Pub. No.: WO2013/110098
PCT Pub. Date: Aug. 1, 2013

(65) Prior Publication Data
US 2014/0299195 A1    Oct. 9, 2014

(30) Foreign Application Priority Data
Jan. 25, 2012 (DE) .......................... 10 2012 100 632

(51) Int. Cl.
*F27B 5/04* (2006.01)
*B22F 3/00* (2006.01)
(Continued)

(52) U.S. Cl.
CPC . *F27B 5/04* (2013.01); *A61C 13/00* (2013.01); *B22F 3/003* (2013.01); *B22F 3/10* (2013.01); *C22C 1/02* (2013.01); *C22C 38/00* (2013.01); *F27B 17/025* (2013.01);
(Continued)

(58) Field of Classification Search
CPC .......... B22F 3/003; B22F 3/10; F27B 17/025; F27B 5/04
USPC ......... 432/247; 419/30, 57; 425/78; 219/390, 219/411
See application file for complete search history.

(56) References Cited

U.S. PATENT DOCUMENTS 2,002,241 A * 5/1935 Forde ...................... F27D 11/02
                                                            219/390
3,295,844 A * 1/1967 Neeley ..................... B22F 3/003
                                                            425/78
(Continued)

FOREIGN PATENT DOCUMENTS

DE    202011005465    8/2011
DE    202011106734    1/2012
(Continued)

OTHER PUBLICATIONS

Multimat2sinter date unknown, Jan. 2011, (admitted prior art).

*Primary Examiner* — Gregory A Wilson
(74) *Attorney, Agent, or Firm* — Volpe and Koenig, P.C.

(57) ABSTRACT

A sintering device (1) for sintering workpieces, in particular dental workpieces, in a shielding gas atmosphere, wherein the sintering device (1) has at least one sintering chamber (2) with at least one gas inlet (3) and at least one gas outlet (4) for a gas exchange in a sintering chamber cavity (5) which is surrounded by the sintering chamber (2), and the sintering device has at least one sintering material cup (6) arranged in the sintering chamber cavity (5) in order to receive the workpiece to be sintered. The sintering device (1) additionally has at least one sintering material cover (7) for covering the workpiece to be sintered in the sintering material cup (6).

16 Claims, 2 Drawing Sheets

(51) Int. Cl.
  *B22F 3/10* (2006.01)
  *A61C 13/00* (2006.01)
  *F27B 17/02* (2006.01)
  *C22C 38/00* (2006.01)
  *F27D 5/00* (2006.01)
  *C22C 1/02* (2006.01)
  *A61C 13/08* (2006.01)
  *C22C 19/07* (2006.01)

(52) U.S. Cl.
  CPC .............. *F27D 5/0043* (2013.01); *A61C 13/08* (2013.01); *B22F 3/1007* (2013.01); *C22C 19/07* (2013.01); *Y10T 137/0318* (2015.04); *Y10T 137/8376* (2015.04)

(56) References Cited

U.S. PATENT DOCUMENTS

| | | | |
|---|---|---|---|
| 5,048,801 A * | 9/1991 | Johnson | B22F 3/003 266/251 |
| 5,432,319 A * | 7/1995 | Indig | A61C 13/20 118/725 |
| 5,604,919 A | 2/1997 | Sterzel et al. | |
| 5,911,102 A | 6/1999 | Takahashi et al. | |
| 6,027,686 A | 2/2000 | Takahashi et al. | |
| 6,696,015 B2 | 2/2004 | Tokuhara et al. | |
| 6,891,140 B2 * | 5/2005 | Sato | C04B 33/36 219/681 |
| 7,767,942 B2 * | 8/2010 | Stephan | C04B 35/42 219/679 |
| 2008/0213119 A1 | 9/2008 | Wolz | |
| 2010/0274292 A1 | 10/2010 | Wolff et al. | |
| 2011/0171589 A1 * | 7/2011 | Ha | F27B 21/04 432/13 |
| 2012/0174404 A1 | 7/2012 | Wolz | |
| 2013/0149186 A1 * | 6/2013 | Hachenberg | B22F 3/003 419/57 |

FOREIGN PATENT DOCUMENTS

| | | |
|---|---|---|
| DE | 202012004493 | 8/2012 |
| DE | 102011056211 | 2/2013 |
| DE | 102012100631 | 7/2013 |
| EP | 0094511 | 11/1983 |
| EP | 0524438 | 1/1993 |
| EP | 1645351 | 4/2006 |
| EP | 1885278 | 1/2009 |
| EP | 2246074 | 11/2010 |
| EP | 2470113 | 8/2013 |
| JP | 5194407 | 8/1976 |
| JP | 56081603 | 7/1981 |
| JP | 58141305 | 8/1983 |
| JP | 05025563 | 2/1993 |
| JP | 06330105 | 11/1994 |
| JP | 2002372373 | 12/2002 |
| WO | 2008021495 | 2/2008 |
| WO | 2009029993 | 3/2009 |
| WO | 2011020688 | 2/2011 |
| WO | 2014047664 | 4/2014 |
| WO | 2014169303 | 10/2014 |
| WO | 2014169304 | 10/2014 |

* cited by examiner

SINTERING DEVICE

BACKGROUND

The present invention relates to a sintering device for sintering workpieces, in particular dental workpieces, in a shielding gas atmosphere, the sintering device having at least one sintering chamber, with at least one gas inlet and at least one gas outlet for gas exchange in a sintering chamber cavity enclosed by the sintering chamber, and at least one sintering material cup, which can be arranged in the sintering chamber cavity and is intended for receiving the workpiece to be sintered.

Sintering devices of the generic type are known for example from WO 2011/020688 A1. They offer the possibility of for example sintering metallic or ceramic workpieces, in particular for the dental sector, in a shielding gas atmosphere, such as for example by using argon. The shielding gas atmosphere serves for preventing oxidation processes on the workpiece during the sintering operation. The shielding gas atmosphere allows the sintering operation to proceed in an oxide-free, or at least oxide-reduced, environment. As a result, discolorations and oxidations of the workpiece, and consequently laborious reworking operations to remove them, are avoided.

SUMMARY

The object of the invention is to improve a sintering device of the generic type to the extent that as high a concentration of shielding gas as possible can be achieved in the region of the workpiece to be sintered.

To achieve this object, the invention provides a sintering device that additionally has at least one sintering material cover for covering the workpiece to be sintered in the sintering material cup.

With the sintering material cover according to the invention, a deoxidizing of the gas flows and a very high concentration of the shielding gas in the region of the workpiece to be sintered are achieved. In addition, this measure also has the effect of keeping the consumption of shielding gas very low. Altogether, the sintering material cover consequently helps to avoid oxidations on the workpiece, and thereby provides an improvement in the surface quality of the workpiece.

The sintering material cover may be configured in the form of a cup or dish. The sintering material cover may, but does not have to, have a cylindrical form. Other forms are also possible. It is preferably provided that the sintering material cover has an opening that is enclosed by a rim of the sintering material cover and can be placed with the rim in the sintering material cup, on a bottom of the sintering material cup. This applies in particular to the time period of the sintering operation. In order that the shielding gas can penetrate well into the partial region of the sintering material cup cavity which is enclosed by the sintering material cover and in which the workpiece to be sintered is actually located, preferred variants of the invention provide that the sintering material cover and/or the sintering material cup has or have at least one gas overflow opening for gas exchange in a sintering cup cavity which is enclosed by the sintering material cover and the sintering cup and is intended for receiving the workpiece. The gas overflow opening or the gas overflow openings may be arranged between the rim of the sintering material cover and the bottom of the sintering material cup. However, other configurations are also possible. For example, lateral holes in the sintering material cover are also possible as gas overflow opening(s). It is in any event favorable if the gas overflow opening(s) is or are arranged near the aforementioned rim of the sintering material cover. In this sense, it is favorable if the gas overflow opening(s) is or are arranged on the side or half of the sintering material cover that is facing the rim mentioned. The side or half of the sintering material cover that is facing away from the rim mentioned is favorably completely closed.

In order to improve further a lowest possible gas consumption and an ideal inflow behavior of the shielding gas into the sintering material cup, preferred configurations of the invention provide that, in an operating position in which the sintering cup is arranged in the sintering chamber cavity of the sintering chamber, a gap, preferably an annular gap, with a gap width of less than or equal to 1 mm is arranged at least in certain regions between the sintering cup and the sintering chamber. This gap is favorably formed between corresponding walls of the sintering material cup and the sintering chamber. It is created at least during the operation or in the operational state of the sintering device. It does not have to be created all the way around to perform its function. It is sufficient if the gap with the stated gap width is formed only in certain regions. However, there should not be any bypass paths for the gas or gas mixture, in which the shielding gas or residual gas can flow past the gap into the sintering material cup or out of it.

Preferred variants provide that at least the sintering chamber and the sintering material cup are formed of at least one metal or of at least one metal alloy. Metals and metal alloys are generally good thermal conductors, so that, during the sintering operation, the thermal energy can be transported more easily from the outside to the workpiece or sintering material to be sintered that is arranged in the sintering chamber cavity. In comparison with the prior art cited at the beginning, in which the sintering chamber and the sintering material cup are made of ceramic, the heat input takes place much more quickly and efficiently. Furthermore, a particularly good homogeneous temperature distribution is achieved. With such sintering devices, heating up rates of greater than 10 kelvins/minute can be achieved. It is equally possible to implement high cooling-down rates, so that the overall sintering times required can be drastically reduced. A further advantage of the metal configuration is the mechanical strength and the plastic behavior, favorable for handling, of metallic sintering devices or corresponding sintering devices that are based on metal alloys. The risk of unwanted destruction of the sintering devices being caused by mechanical influences is greatly reduced. In addition, it is also possible with such sintering devices to achieve higher temperatures during the sintering operation, that is to say in particular temperatures above 1200° C., without the sintering device being damaged as a result. Thus, for example, when sintering CoCrMo (cobalt-chromium-molybdenum) alloys with sintering temperatures greater than 1250° C., a very high density of the end product or sintered workpiece can be achieved. The remaining residual porosity decreases significantly with increasing sintering temperature, which benefits the final density, and consequently the mechanical strength, of the finished sintered workpiece. As a result, apart from the increase in efficiency in the form of the speed of the process, the quality of the finished sintered workpiece is also increased.

The sintering material cover may be formed of various materials. Thus, it is also possible for the sintering material cover to be made with or of ceramic material, such as for example alumina or zirconia. Furthermore, sintering material covers with or of silicon carbide or quartz glass may also be used. However, the sintering material cover preferably is formed of at least one metal or at least one metal alloy.

In principle, it is favorable if the metals or metal alloys used make sintering possible at temperatures greater than 1200° C. (Celsius). Furthermore, metals or metal alloys that ensure the highest possible heating-up and cooling-down rates, preferably greater than 10 kelvins/minute, in a sustained and reproducible way should be chosen. Furthermore, it is favorable if all of the components of the sintering device have substantially the same coefficient of thermal expansion. In this sense, preferred variants of the invention provide that at least the sintering chamber and the sintering cup and the sintering material cover, preferably the entire sintering device, is formed or comprised of the same material or the same metal alloy.

Metal alloys with iron, chromium and/or aluminum are used particularly preferably for forming the components mentioned of the sintering device. These metal alloys may consist exclusively of corresponding proportions of iron, chromium and/or aluminum. They may, however, also be iron-chromium-aluminum alloys that also have other constituents. Other suitable metals or metal alloys can of course also be used.

With sintering devices according to the invention, in particular metallic workpieces or else for example ceramic workpieces may be sintered.

As in the prior art, argon may be used as the shielding gas. Of course, other suitable gases or noble gases may also be used as the shielding gas. To build up the shielding gas atmosphere in the sintering chamber cavity, the sintering chamber has at least one gas inlet for the introduction of the gas or gas mixture forming the shielding gas atmosphere and at least one gas outlet for the flowing away of the displaced residual gas or shielding gas from the sintering chamber cavity. The gas outlet and gas inlet are favorably formed as separate overflow openings. However, integrated configurations, in which for example a gas inlet is also used as a gas outlet, are also conceivable.

The sintering chamber enclosing the sintering chamber cavity is favorably formed at least as two parts or else has more than two parts. Two-part configurations may include for example a sintering chamber base part and a sintering chamber top part. For the introduction of the workpiece to be sintered and also for its removal, sintering chamber top parts and sintering chamber base parts can be separated from each other, whereas during the sintering operation they form an outwardly closed unit in the form of the sintering chamber. Generally, that is to say also independently of the question of the number of parts from which the sintering chamber is formed, the sintering chamber should form a unit that is outwardly closed, at least in the operating state, apart from the gas inlet and/or gas outlet. The closed form allows sufficient gas-tightness to be achieved.

Apart from the sintering device according to the invention, the invention also relates to a method for sintering workpieces, in particular dental workpieces, in a shielding gas atmosphere with a sintering device according to the invention, the workpiece to be sintered being arranged during the sintering operation in the sintering material cup of the sintering device and the sintering material cup being arranged in the sintering chamber cavity of the sintering chamber, and the workpiece to be sintered being covered by the sintering material cover. The covering of the workpiece to be sintered in the sintering material cup by the sintering material cover achieves the effect already mentioned of increasing the shielding gas concentration in the direct vicinity of the workpiece to be sintered, with at the same time low shielding gas consumption.

BRIEF DESCRIPTION OF THE DRAWINGS

Further features and advantages of preferred configurations according to the invention are explained on the basis of the variant of a sintering device that is shown in the figures, in which.

DETAILED DESCRIPTION OF THE PREFERRED EMBODIMENTS

Figure 1:
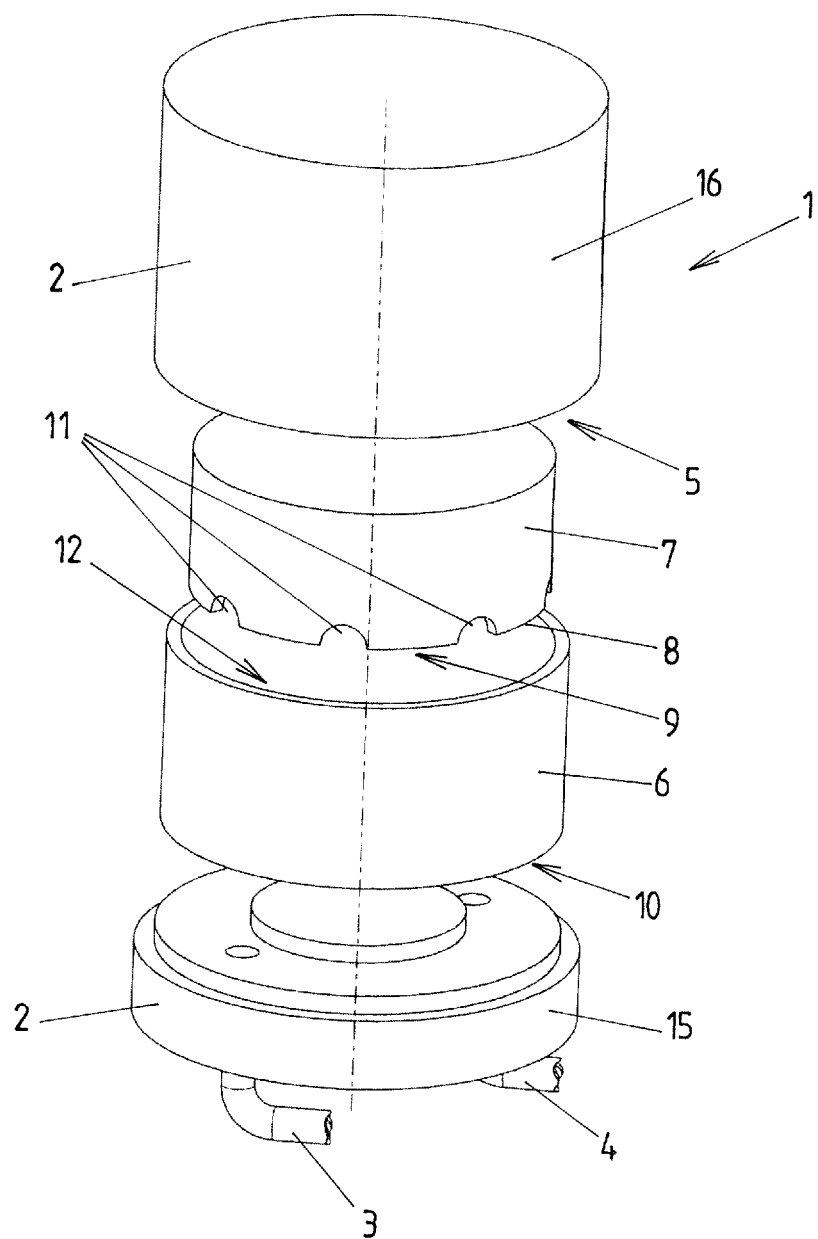
FIG. 1 shows the sintering device in an exploded representation.

In the variant of the invention that is shown in FIG. 1 in an exploded representation, the sintering chamber 2 of the sintering device 1 is formed as two parts. It has a sintering chamber base part 15 and a sintering chamber top part 16. In the operating position that is shown in section in FIG. 2, the sintering chamber base part 15 and the sintering chamber top part 16 may be connected to each other in such a way that overall an outwardly closed-off, sufficiently gastight structure is achieved. Shielding gas, such as for example argon, can penetrate through the gas inlet 3 into the sintering chamber cavity 5 of the sintering chamber 2 that is enclosed by the sintering chamber base part 15 and the sintering chamber top part 16. The displaced residual gas or shielding gas can then leave the sintering chamber cavity 5 again through the gas outlet 4. As already explained at the beginning, the gas inlet 3 and the gas outlet 4 may, as shown here, be formed separately from each other. They may be single or multiple gas inlets or gas outlets. Gas inlets and outlets 3, 4 may have the same or different opening cross sections. They in any case allow a flushing of the sintering chamber cavity 5 and a displacement of the oxygen present there, so that the sintering operation can be carried out in an oxide-free, or at least oxide-reduced, shielding gas atmosphere. Argon, for example, but also other suitable gases or noble gases come into consideration as shielding gases.

Figure 2:
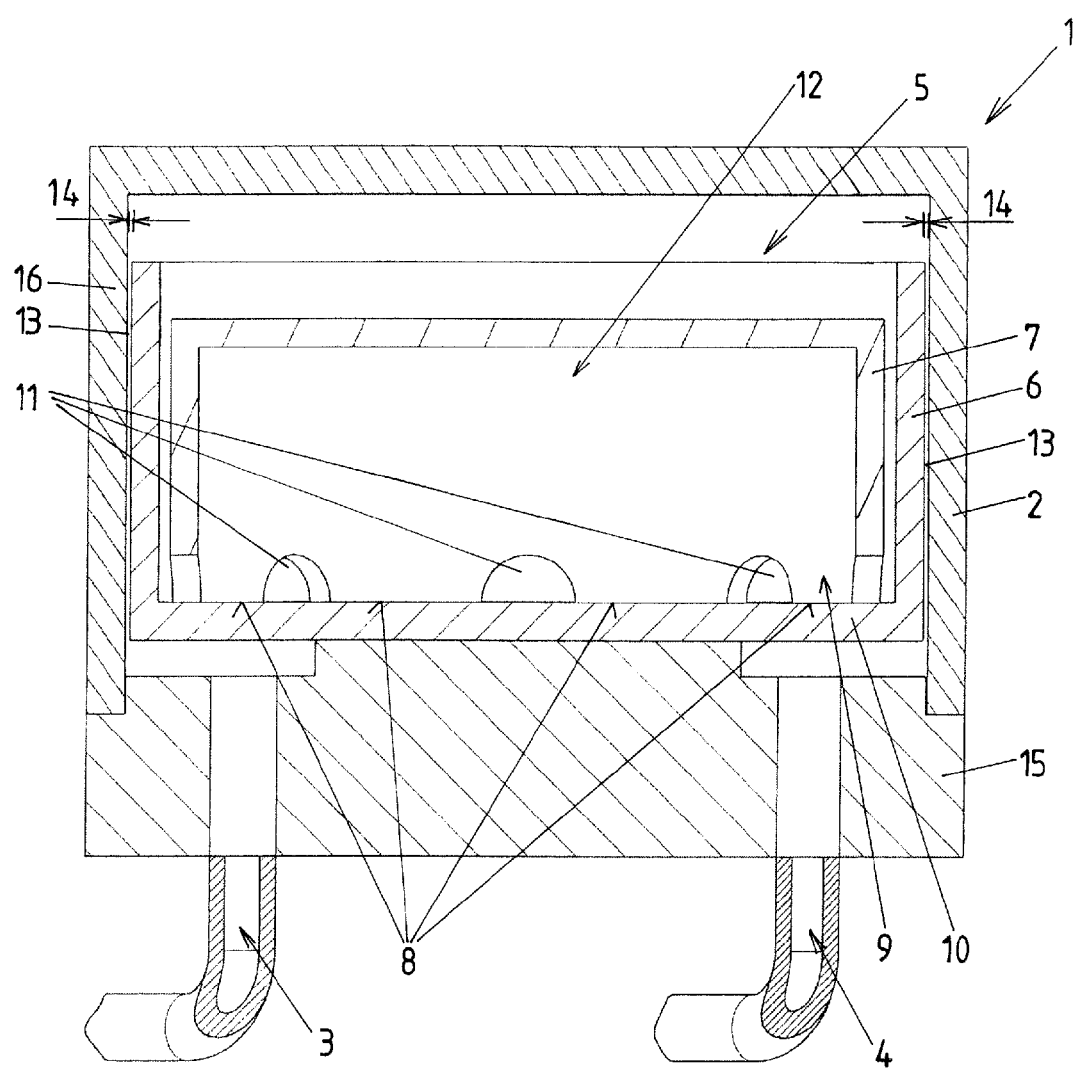
FIG. 2 shows a vertical section through the sintering device in the operating position.

In the operating position according to FIG. 2, the sintering material cup 6, in which the workpiece to be sintered (not represented here) is placed during the sintering operation, is located in the sintering chamber cavity 5. The sintering material cup 6 has the advantage that the generally heavier shielding gas can collect in it, while the generally lighter oxygen is displaced out of the sintering material cup. In the operating position shown, the sintering material cup 6 rests with its bottom 10 on the sintering chamber base part 15, but without thereby blocking the paths from the gas inlet 3 to the gas outlet 4 completely.

The walls of the sintering chamber 2, here the sintering chamber top part 16, and of the sintering material cup 6 are favorably dimensioned such that, at least in certain regions, there is a gap 13 between them, which has a gap width 14 of less than or equal to 1 mm. In the exemplary embodiment shown, this gap 13 is of an annular configuration and surrounds the side walls of the sintering material cup 6 that are formed like the shell of a cylinder. The gap 13 is outwardly surrounded or bounded by outer walls of the sintering chamber 2 in the form of the shell of a cylinder.

In order to increase as far as possible the concentration of shielding gas in the region of the workpiece or sintering material (not represented here), according to the invention, in the exemplary embodiment shown, a sintering material cover 7 is arranged in the sintering material cup cavity 12 during the sintering operation, that is to say in the position that is shown in FIG. 2. During the sintering operation, the workpiece to be sintered, which is not represented here, is located between the bottom 10 of the sintering material cup 6 and the sintering material cover 7. In the operating position shown, the sintering material cover 7 is placed with its rim 8, which surrounds the opening 9, on the bottom 10 of the sintering material cup 6. Shielding gas can penetrate into this region and residual gas can flow out through the gas overflow openings 11.

In order to put into operation the sintering device 1 that is represented in the exemplary embodiment shown, the sintering material cup 6 is placed with its bottom 10 on the sintering chamber base part 15. Subsequently, the workpiece to be sintered is placed onto the bottom 10 or introduced into the sintering material cup cavity 12. After that, the sintering material cover 7 is fitted over the workpiece to be sintered, so that the rim 8 stands on the bottom 10. Subsequently, the sintering chamber 2 is closed, in that the sintering chamber top part 16 is placed onto the sintering chamber base part 15, whereby the operational position that is shown in FIG. 2 is obtained. Subsequently, the entire sintering chamber cavity 5, and consequently the sintering material cup cavity 12 in particular, can be flushed with shielding gas, until the required shielding gas atmosphere has been established with the desired concentration. For this purpose, the shielding gas is introduced by way of the gas inlet 3 and the displaced residual gas and shielding gas is carried away by way of the gas outlet 4. The gases that are not the shielding gas and have to be displaced during the sintering operation are referred to as residual gas. Flushing with shielding gas is performed during the entire sintering operation. Residual gases, but also shielding gas, then flow out through the gas outlet. The sintering operation is initiated by appropriate heating of the sintering device 1 from the outside. After corresponding cooling down at the end of the sintering, the entire structure can be disassembled again in the reverse sequence, and the sintered workpiece can be removed.

KEY TO REFERENCE SIGNS

1 Sintering device
 2 Sintering chamber
 3 Gas inlet
 4 Gas outlet
 5 Sintering chamber cavity
 6 Sintering material cup
 7 Sintering material cover
 8 Rim
 9 Opening
10 Bottom
11 Gas overflow opening
12 Sintering material cup cavity
13 Gap
14 Gap width
15 Sintering chamber base part
16 Sintering chamber top part

The invention claimed is:

1. A sintering device for sintering workpieces, in a shielding gas atmosphere, the sintering device comprising at least one sintering chamber, with at least one gas inlet and at least one gas outlet for gas exchange in a sintering chamber cavity enclosed by the sintering chamber, and at least one sintering material cup arranged in the sintering chamber cavity that is adapted to receive the workpiece to be sintered, and at least one sintering material cover adapted to cover the workpiece to be sintered in the sintering material cup, and the sintering material cover includes an opening that is enclosed by a rim of the sintering material cover and is placed with the rim in the sintering material cup, on a bottom of the sintering material cup.

2. The sintering device as claimed in claim 1, wherein at least one of the sintering material cover or the sintering material cup has at least one gas overflow opening for gas exchange in a sintering material cup cavity enclosed by the sintering material cover and the sintering material cup adapted to receive the workpiece to be sintered.

3. The sintering device as claimed in claim 2, wherein the at least one gas overflow opening is located between the rim of the sintering material cover and the bottom of the sintering material cup.

4. The sintering device as claimed in claim 1, wherein at least the sintering chamber and the sintering material cup are formed of at least one metal or of at least one metal alloy.

5. The sintering device as claimed in claim 4, wherein the metal alloy includes at least one of iron, chromium or aluminum as at least one alloying component.

6. The sintering device as claimed in claim 1, wherein the sintering material cover is formed of at least one metal or at least one metal alloy.

7. The sintering device as claimed in claim 6, wherein the metal alloy includes at least one of iron, chromium or aluminum as at least one alloying component.

8. The sintering device as claimed in claim 1, wherein the entire sintering device is formed of at least one metal or of at least one metal alloy.

9. The sintering device as claimed in claim 8, wherein the metal alloy includes at least one of iron, chromium or aluminum as at least one alloying component.

10. The sintering device as claimed in claim 1, wherein at least the sintering chamber and the sintering material cup and the sintering material cover are formed or comprised of the same metal or the same metal alloy.

11. The sintering device as claimed in claim 10, wherein the metal alloy includes at least one of iron, chromium or aluminum as at least one alloying component.

12. The sintering device as claimed in claim 1, wherein the sintering material cover comprises or is formed of ceramic material.

13. The sintering device as claimed in claim 12, wherein the ceramic material comprises at least one of alumina, zirconia, silicon carbide, or quartz glass.

14. The sintering device as claimed in claim 1, wherein, in an operating position in which the sintering material cup is arranged in the sintering chamber cavity of the sintering chamber, a gap with a gap width of less than or equal to 1 mm is arranged at least in certain regions between the sintering material cup and the sintering chamber.

15. The sintering device as claimed in claim 14, wherein the gap is an annular gap.

16. A method for sintering workpieces in a shielding gas atmosphere with a sintering device as claimed in claim 1, comprising arranging the workpiece to be sintered during the sintering operation in the sintering material cup of the sintering device and arranging the sintering material cup in the sintering chamber cavity of the sintering chamber, and covering the workpiece to be sintered with the sintering material cover.

* * * * *